(12) United States Patent
Sugimoto

(10) Patent No.: US 8,580,288 B2
(45) Date of Patent: Nov. 12, 2013

(54) AGRICULTURAL OR HORTICULTURAL FUNGICIDE COMPOSITION AND ITS USE FOR CONTROLLING PLANT PATHOGENS

(75) Inventor: Koji Sugimoto, Kusatsu (JP)

(73) Assignee: Ishihara Sangyo Kaisha, Ltd, Osaka (JP)

( * ) Notice: Subject to any disclaimer, the term of this patent is extended or adjusted under 35 U.S.C. 154(b) by 0 days.

(21) Appl. No.: 13/382,478

(22) PCT Filed: Jul. 6, 2010

(86) PCT No.: PCT/JP2010/061736
§ 371 (c)(1),
(2), (4) Date: Jan. 5, 2012

(87) PCT Pub. No.: WO2011/004901
PCT Pub. Date: Jan. 13, 2011

(65) Prior Publication Data
US 2012/0108644 A1 May 3, 2012

(30) Foreign Application Priority Data

Jul. 6, 2009 (JP) ................................. 2009-160257

(51) Int. Cl.
*A01N 25/32* (2006.01)

(52) U.S. Cl.
USPC ........... 424/406; 424/405; 424/409; 514/398; 514/412

(58) Field of Classification Search
None
See application file for complete search history.

(56) References Cited

U.S. PATENT DOCUMENTS

2007/0135497 A1* 6/2007 Mitani et al. .................. 514/357
2010/0240619 A1* 9/2010 Gregory et al. ............... 514/154

FOREIGN PATENT DOCUMENTS

| CN | 101312649 A | 11/2008 |
| EP | 0 337 103 A2 | 10/1989 |
| JP | 1-131163 A | 5/1989 |

OTHER PUBLICATIONS

State Intellectual Property Office of P.R. China, Office Action dated Mar. 12, 2013, issued in counterpart Chinese Patent Application No. 201080030388.X.

* cited by examiner

*Primary Examiner* — Neil Levy
(74) *Attorney, Agent, or Firm* — Sughrue Mion, PLLC

(57) ABSTRACT

The present invention provides a composition in which a fungicidal effect against a cultivated crop infected by a plant pathogen is stable and highly active. An excellent agricultural or horticultural fungicide composition for controlling a plant pathogen is provided by using (a) at least one imidazole compound represented by formula (I):

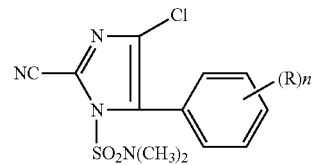

wherein R represents a C1-6 alkyl group or a C1-6 alkoxy group; and n represents an integer of 1 to 5 and (b) folpet as active ingredients; by combination as compared to a single use of each compound, and a plant pathogen is thereby controlled.

5 Claims, No Drawings

AGRICULTURAL OR HORTICULTURAL FUNGICIDE COMPOSITION AND ITS USE FOR CONTROLLING PLANT PATHOGENS

TECHNICAL FIELD

The present invention relates to an agricultural or horticultural fungicide composition wherein a control effect against a plant pathogen, especially a preventive and/or therapeutic effect against a plant pathogen, is markedly improved; and a method for controlling a plant pathogen using thereof.

BACKGROUND ART

Patent Literature 1 discloses that an imidazole compound, one of the active ingredients in the agricultural or horticultural fungicide composition of the present invention is useful for a harmful bio-organism controlling agent. In addition, it also discloses that if necessary, the composition can be mixed with or used in combination with other fungicides, and as one example of them, N-(trichloromethylsulphenyl)phthalimide is described. However, Patent Literature 1 does not disclose any specific data using the imidazole compound mixed with the above compound.

Furthermore, Patent Literature 2 discloses folpet as an agricultural or horticultural fungicide.

CITATION LIST

Patent Literature

Patent Literature 1 Japanese Unexamined Patent Application Publication No. 1989-131163
Patent Literature 2 U.S. Pat. No. 2,553,770

SUMMARY OF INVENTION

Technical Problem

Since an imidazole compound represented by the following formula (I) is slightly insufficient in a control effect against some of specific plant pathogens or is relatively short in residual efficacy, it does not practically exhibit a sufficient control effect against a plant pathogen in some conditions for application.

Solution to Problem

As a result of investigations to solve the above-described problem, the present inventors have found that use of an imidazole compound represented by the following formula (I) in combination with folpet exhibits unpredictable and excellent control effect against a plant pathogen as compared to a single use of each compound, and have completed the present invention.

The present invention relates to an agricultural or horticultural fungicide composition comprising (a) at least one imidazole compound represented by formula (I):

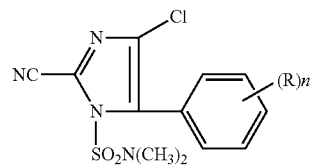

wherein R represents a C1-6 alkyl group or a C1-6 alkoxy group; and
n represents an integer of 1 to 5,
and (b) folpet as active ingredients. And the present invention relates to a method for controlling a plant pathogen, comprising applying the above mentioned composition to a plant or soil. In addition, the present invention relates to a method for controlling a plant pathogen, comprising applying an effective amount of (a) at least one imidazole compound represented by formula (I) and an effective amount of (b) folpet to a plant or soil.

In formula (I), the C1-6 alkyl group or the alkyl moiety of the C1-6 alkoxy group as represented by R includes an alkyl group having 1 to 6 carbon atoms, such as methyl, ethyl, propyl, butyl, pentyl or hexyl, which may have either a straight chain or a branched chain. When n is 2 or greater, the plural R5 may be the same or different.

Examples of the imidazole compounds represented by formula (I) include the following compounds:
4-chloro-2-cyano-1-dimethylsulfamoyl-5-(4-methylphenyl)imidazole (Compound No. 1);
4-chloro-2-cyano-1-dimethylsulfamoyl-5-(4-methoxyphenyl)imidazole (Compound No. 2);
4-chloro-2-cyano-1-dimethylsulfamoyl-5-(4-ethylphenyl)imidazole (Compound No. 3); and
4-chloro-2-cyano-1-dimethylsulfamoyl-5-(3-methyl-4-methoxyphenyl)imidazole (Compound No. 4).

In addition, Compound No. 1 is known as Cyazofamid in terms of a common name.

Folpet which is used as an active ingredient (b) of the present invention is N-(trichloromethanesulphenyl)phthalimide.

Since an agricultural or horticultural fungicide composition comprising (a) at least one selected from the imidazole compound represented by the above formula (I) and (b) folpet as active ingredients (hereinafter referred to as the composition of the present invention) exhibits an excellent fungicidal activity by applying a cultivated crop, for example, vegetables, such as cucumbers, tomatoes, and eggplants; cereals such as rice and wheat; peas; fruit trees, such as apples, pears, grapes and citrus; and potatoes, which is infected or have a possibility to be infected by harmful pathogens, it is desirable for controlling diseases such as powdery mildew, downy mildew, anthracnose, gray mold, common green mold, scab, leaf spot disease, bacterial blight, black spot, black spot disease, rot overnight, blight, ring spot, blast, sheath blight, seedling blight and southern blight. In addition, the composition of the present invention exhibits an excellent control effect against soil-borne diseases caused by plant pathogens such as *Fusarium, Rhizoctonia, Verticillium, Purazumodiohora, Pythium*. The composition of the present invention has a long residual efficacy and especially it is excellent in a preventive effect.

The composition of the present invention exhibits a control effect against a disease, such as rice blast; rice sheath blight; cucumber anthracnose; downy mildew of cucumbers, melons, cabbages, Chinese cabbages, onions, pumpkins, grapes;

powdery mildew of wheat, barley, cucumbers; blight of potatoes, red peppers, sweet peppers, watermelons, pumpkins, tobaccos, tomatoes; wheat Septoria disease; tomato ring spot; citrus melanose; citrus common green mold; pear scab; apple Alternaria blotch; onion white tip; watermelon brown rot; various gray mold; various crown rot; various rust; and various bacterial blight, and various soil-borne diseases caused by plant pathogenic fungi, such as *Fusarium, Pythium, Rhizoctonia*, and *Verticillium*. In addition, the composition of the present invention exhibits an excellent control effect against diseases causing by *Plasmodiophora*. More specifically, the composition exhibits an especially excellent control effect against diseases such as blight of potatoes, red peppers, sweet peppers, watermelons, pumpkins, tobaccos, tomatoes; downy mildew of cucumbers, melons, cabbages, Chinese cabbages, onions, pumpkins, grapes; and Pythium disease, bacterial shoot blight and leaf blight (brown patch and large patch) of grass.

The active ingredients which constitute the composition of the present invention can be formulated into a variety of forms, such as emulsifiable concentrates, dustable powders, wettable powders, soluble concentrates, granules, suspension concentrates, etc., together with various adjuvants, as in conventional agricultural preparations. The active ingredients, (a) at least one selected from the imidazole compound of the above formula (I) and (b) folpet, and other specific compounds may be mixed and formulated, or each of them may be separately formulated and then mixed together. Upon use, the preparation may be used as such or as diluted with an appropriate diluent, e.g., water, to a predetermined concentration. Examples of the adjuvants which can be used include carriers, emulsifying agents, suspending agents, thickeners, stabilizers, dispersants, spreaders, wetting agents, penetrating agents, antifreezing agents, antifoaming agents and the like. These adjuvants are added appropriately, if necessary. The carriers are classified into solid carriers and liquid carriers. The solid carriers include animal and vegetable powders (e.g., starch, sugar, cellulose powders, cyclodextrin, activated charcoal, soybean powders, wheat powders, chaff powders, wood powders, fish powders, powdery milk, etc.); mineral powders (e.g., talc, kaolin, bentonite, organic bentonite, calcium carbonate, calcium sulfate, sodium hydrogencarbonate, zeolite, diatomaceous earth, white carbon, clay, alumina, silica, sulfur powder, slaked lime, etc.); and the like. Examples of the liquid carriers include water, vegetable oils (e.g., soybean oil, cotton seed oil), animal oils (e.g., beef tallow, whale oil, etc.), alcohols (e.g., ethyl alcohol, ethylene glycol, etc.), ketones (e.g., acetone, methyl ethyl ketone, methyl isobutyl ketone, isophorone, etc.), ethers (e.g., dioxane, tetrahydrofuran, etc.), aliphatic hydrocarbons (e.g., kerosene, lamp oil, liquid paraffin, etc.), aromatic hydrocarbons (e.g., toluene, xylene, trimethylbenzene, tetramethylbenzene, cyclohexane, solvent naphtha, etc.), halogenated hydrocarbons (e.g., chloroform, chlorobenzene, etc.), acid amides (e.g., N-methyl-2-pyrrolidone, N,N-dimethylformamide, N,N-dimethylacetamide, etc.), esters (e.g., ethyl acetate, fatty acid glycerine esters, etc.), nitriles (e.g., acetonitrile, etc.), sulfur-containing compounds (e.g., dimethyl sulfoxide, etc.) and the like. Examples of the spreaders include sodium alkylsulfate, sodium alkylbenzene sulfonate, sodium lignin sulfonate, polyoxyethylene glycol alkyl ether, polyoxyethylene lauryl ether, polyoxyethylene alkyl aryl ether, polyoxyethylene sorbitan fatty acid ester and the like.

In addition, the composition of the present invention can be mixed with other agricultural chemicals, such as a fungicide, an insecticide, a miticide, a nematocide, a soil insect pesticide, an antivirus agent, an attractant, a herbicide, a plant growth regulating agent and in this case, further excellent effect is sometimes exhibited.

The active ingredient compounds of the fungicide in the above-mentioned other agricultural chemicals include, for example, (by common names, some of them are still in an application stage, or test codes of Japan Plant Protection Association):

anilinopyrimidine compounds, such as mepanipyrim, pyrimethanil, and cyprodinil;

a triazoropyrimidine compound, such as 5-chloro-7-(4-methylpiperidin-1-yl)-6-(2,4,6-trifluorophenyl)[1,2,4]triazolo[1,5-a]pyrimidine;

pyridinamine compounds, such as fluazinam;

azole compounds, such as triadimefon, bitertanol, triflumizole, etaconazole, propiconazole, penconazole, flusilazole, myclobutanil, cyproconazole, tebuconazole, hexaconazole, furconazole-cis, prochloraz, metconazole, epoxiconazole, tetraconazole, oxpoconazole fumarate, sipconazole, prothioconazole, triadimenol, flutriafol, difenoconazole, fluquinconazole, fenbuconazole, bromuconazole, diniconazole, tricyclazole, probenazole, simeconazole, pefurazoate, ipconazole and imibenconazole;

quinoxaline compounds, such as quinomethionate;

dithiocarbamate compounds, such as maneb, zineb, mancozeb, polycarbamate, metiram, propineb and thiram;

organic chlorine compounds, such as fthalide, chlorothalonil and quintozene;

imidazole compounds, such as benomyl, thiophanate-methyl, carbendazim, thiabendazole and fuberiazole;

cyanoacetamide compounds, such as cymoxanil;

anilide compounds, such as metalaxyl, metalaxyl-M, mefenoxam, oxadixyl, ofurace, benalaxyl, benalaxyl-M (another name: kiralaxyl, chiralaxyl), furalaxyl, cyprofuram, carboxin, oxycarboxin, thifluzamide, boscalid, bixafen, isotianil, tiadinil and sedaxane;

sulfamide compounds, such as dichlofluanid;

copper compounds, such as cupric hydroxide and oxine copper;

isoxazole compounds, such as hymexazol;

organophosphorus compounds, such as fosetyl-Al, tolclofos-methyl, S-benzyl O,O-diisopropylphosphorothioate, O-ethyl S,S-diphenylphosphorodithioate, aluminum ethylhydrogen phosphonate, edifenphos, and iprobenfos;

phthalimide compounds, such as captan and captafol;

dicarboximide compounds, such as procymidone, iprodione and vinclozolin;

benzanilide compounds, such as flutolanil and mepronil;

amide compounds, such as penthiopyrad, mixture of 3-(difluoromethyl)-1-methyl-N-[(1RS,4SR,9SR)-1,2,3,4-tetrahydro-9-isopropyl-1,4-methanonaphthalen-5-yl]pyrazole-4-carboxamide and 3-(difluoromethyl)-1-methyl-N-[(1RS,4SR,9SR)-1,2,3,4-tetrahydro-9-isopropyl-1,4-methanonaphthalen-5-yl]pyrazole-4-carboxamide (isopyrazam), silthiopham and fenoxanil;

benzamide compounds, such as fluopyram and zoxamide;

piperazine compounds, such as triforine;

pyridine compounds, such as pyrifenox;

carbinol compounds, such as fenarimol;

piperidine compounds, such as fenpropidine;

morpholine compounds, such as fenpropimorph and tridemorph;

organotin compounds, such as fentin hydroxide and fentin acetate;

urea compounds, such as pencycuron;

cinnamic acid compounds, such as dimethomorph and flumorph;

phenylcarbamate compounds, such as diethofencarb;

cyanopyrrole compounds, such as fludioxonil and fenpiclonil;

strobilurin compounds, such as azoxystrobin, kresoxim-methyl, metominostrobin, trifloxystrobin, picoxystrobin, oryzastrobin, dimoxystrobin, pyraclostrobin, and fluoxastrobin;

oxazolidinone compounds, such as famoxadone;

thiazolecarboxamide compounds, such as ethaboxam;

valinamide compounds, such as iprovalicarb and benthiavalicarb-isopropyl;

acylamino acid compounds, such as methyl N-(isopropoxycarbonyl)-L-valyl-(3RS)-3-(4-chlorophenyl)-β-alaninate (valiphenalate);

imidazolinone compounds, such as fenamidone;

hydroxyanilide compounds, such as fenhexamid;

benzenesulfonamide compounds, such as flusulfamide;

oxime ether compounds, such as cyflufenamid;

anthraquinone compounds;

crotonic compounds;

antibiotics, such as validamycin, kasugamycin and polyoxins;

guanidine compounds, such as iminoctadine and dodine;

quinoline compounds, such as 6-tert-butyl-8-fluoro-2,3-dimethylquinolin-4-yl acetate (tebufloquin);

thiazolidine compounds, such as (z)-2-(2-fluoro-5-(trifluoromethyl)phenylthio)-2-(3-(2-methoxyphenyl)thiazolidin-2-yliden)acetonitrile (flutianil);

and other compounds, such as pyribencarb, isoprothiolane, pyroquilon, diclomezine, quinoxyfen, propamocarb hydrochloride, chloropicrin, dazomet, metam-sodium, nicobifen, metrafenone, UBF-307, diclocymet, proquinazid, amisulbrom (another name: amibromdole), 3-(2,3,4-trimethoxy-6-methylbenzoyl)-5-chloro-2-methoxy-4-methylpyridine, 4-(2,3,4-trimethoxy-6-methylbenzoyl)-2,5-dichloro-3-frifluoromethylpyridine, 4-(2,3,4-trimethoxy-6-methylbenzoyl)-2-chloro-3-trifluoromethyl-5-methoxypyridine, mandipropamid, fluopicolide, carpropamid, meptyldinocap, N-[(3',4'-dichloro-1,1-dimethyl)phenacyl]-3-trifluoromethyl-2-pyridine carboxamide, N-[(3',4'-dichloro-1,1-dimethyl)phenacyl]-3-methyl-2-thiophene carboxamide, N-[(3',4'-dichloro-1,1-dimethyl)phenacyl]-1-methyl-3-trifluoromethyl-4-pyrazole carboxamide, N[[2'-methyl-4'-(2-propyloxy)-1,1-dimethyl]phenacyl]-3-trifluoromethyl-2-pyridine carboxamide, N-[[2'-methyl-4'-(2-propyloxy)-1,1-dimethyl]phenacyl]-3-methyl-2-thiophene carboxamide, N[[2'-methyl-4'-(2-propyloxy)-1,1-dimethyl]phenacyl]-1-methyl-3-trifluoromethyl-4-pyrazole carboxamide, N-[[4'-(2-propyloxy)-1,1-dimethyl]phenacyl]-3-trifluoromethyl-2-pyridine carboxamide, N-[[4'-(2-propyloxy)-1,1-dimethyl]phenacyl]-3-methyl-2-thiophene carboxamide, N-[[4'-(2-propyloxy)-1,1-dimethyl]phenacyl]-1-methyl-3-trifluoromethyl-4-pyrazole carboxamide, N-[[2'-methyl-4'-(2-pentyloxy)-1,1-dimethyl]phenacyl]-3-trifluoromethyl-2-pyridine carboxamide, N-[[4'-(2-pentyloxy)-1,1-dimethyl]phenacyl]-3-trifluoromethyl-2-pyridine carboxamide, ferimzone, spiroxamine, S-2188 (fenpyrazamine), S-2200, ZF-9646, BCF-051, BCM-061 and BCM-062.

The active ingredient compounds of an insect pest control agents, such as the insecticide, the miticide, the nematicide or the soil insect pesticide in the above-mentioned other agricultural chemicals, include, for example, (by common names, some of them are still in an application stage, or test codes of Japan Plant Protection Association):

organic phosphate compounds, such as profenofos, dichlorvos, fenamiphos, fenitrothion, EPN, diazinon, chlorpyrifos, chlorpyrifos-methyl, acephate, prothiofos, fosthiazate, cadusafos, dislufoton, isoxathion, isofenphos, ethion, etrimfos, quinalphos, dimethylvinphos, dimethoate, sulprofos, thiometon, vamidothion, pyraclofos, pyridaphenthion, pirimiphos-methyl, propaphos, phosalone, formothion, malathion, tetrachlorvinp hos, chlorfenvinphos, cyanophos, trichlorfon, methidathion, phenthoate, ESP, azinphos-methyl, fenthion, heptenophos, methoxychlor, parathion, phosphocarb, demeton-S-methyl, monocrotophos, methamidophos, imicyafos, parathion-methyl, terbufos, phosphamidon, phosmet and phorate;

carbamate compounds, such as carbaryl, propoxur, aldicarb, carbofuran, thiodicarb, methomyl, oxamyl, ethiofencarb, pirimicarb, fenobucarb, carbosulfan, benfuracarb, bendiocarb, furathiocarb, isoprocarb, metolcarb, xylylcarb, XMC and fenothiocarb;

nereistoxin derivatives, such as cartap, thiocyclam, bensultap and thiosultap-sodium;

organic chlorine compounds, such as dicofol, tetradifon, endosulfan, dienochlor and dieldrin;

organic metal compounds, such as fenbutatin oxide and cyhexatin;

pyrethroid compounds, such as fenvalerate, permethrin, cypermethrin, deltamethrin, cyhalothrin, tefluthrin, ethofenprox, flufenprox, cyfluthrin, fenpropathrin, flucythrinate, fluvalinate, cycloprothrin, lambda-cyhalothrin, pyrethrins, esfenvalerate, tetramethrin, resmethrin, protrifenbute, bifenthrin, zeta-cypermethrin, acrinathrin, alpha-cypermethrin, allethrin, gamma-cyhalothrin, theta-cypermethrin, tau-fluvalinate, tralomethrin, profluthrin, beta-cypermethrin, beta-cyfluthrin, metofluthrin, phenothrin and flumethrin;

benzoylurea compounds, such as diflubenzuron, chlorfluazuron, teflubenzuron, flufenoxuron, triflumuron, hexaflumuron, lufenuron, novaluron, noviflumuron, bistrifluoron, and fluazuron;

juvenile hormone-like compounds, such as methoprene, pyriproxyfen, fenoxycarb and diofenolan;

pyridazinone compounds, such as pridaben;

pyrazole compounds, such as fenpyroximate, fipronil, tebufenpyrad, ethiprole, tolfenpyrad, acetoprole, pyrafluprole and pyriprole;

neonicotinoids, such as imidacloprid, nitenpyram, acetamiprid, thiacloprid, thiamethoxam, clothianidin, nidinotefuran, dinotefuran and nithiazine;

hydrazine compounds, such as tebufenozide, methoxyfenozide, chromafenozide and halofenozide;

pyridine compounds, such as flonicamid;

tetronic acid compounds, such as spirodiclofen;

strobilurin compounds, such as fluacrypyrim;

pyrimidinamine compounds, such as flufenerim;

dinitro compounds; organic sulfur compounds; urea compounds; triazine compounds; hydrazone compounds;

other compounds, such as buprofezin, hexythiazox, amitraz, chlordimeform, silafluofen, triazamate, pymetrozine, pyrimidifen, chlorfenapyr, indoxacarb, acequinocyl, etoxazole, cyromazine, 1,3-dichloropropene, diafenthiuron, benclothiaz, bifenazate, spiromesifen, spirotetramat, propargite, clofentezine, metaflumizone, flubendiamide, cyflumetofen, chlorantraniliprole, cyenopyrafen, pyrifluquinazon, fenazaquin, amidoflumet, chlorobenzoate, sulfluramid, hydramethylnon, metaldehyde, HGW-86, AKD-1022, ryanodine, pyridalyl and verbutin; and the like. Further, it may be used in combination with or together with microbial agricultural chemicals, such as *Bacillus thuringiensis aizawai*, *Bacillus thuringiensis kurstaki*, *Bacillus thuringiensis israelensis*, *Bacillus thuringiensis japonensis*, *Bacillus thuringiensis tenebrionis*, insecticidal crystal proteins produced by *Bacillus thuringiensis*, insect viruses, etomopathogenic fungi, and nematophagous fungi; antibiotics or semisynthetic antibiotics, such as avermectin, emamectin benzoate, milbemectin, milbemycin, spinosad, ivermectin, lepimectin, DE-175, abamectin, emamectin and spinetoram; natural products, such as azadirachtin and rotenone; and repellents, such as deet.

In the composition of the present invention, a suitable weight ratio of (a) at least one imidazole compound to (b) folpet is usually from 1:10,000 to 10,000:1, preferably from 1:2,000 to 2,000:1.

The present invention also relates to a method for controlling a plant pathogen comprising applying the composition of the present invention to a plant or soil. Concentration of the active ingredient to be used for the composition of the present invention varies depending on differences in objective crops, use method, preparation form, application amount, application time, kinds of harmful pathogens and the like, and cannot necessarily be defined. However, in foliage treatment or soil-drenching treatment, as an active ingredient concentration, the imidazole compound of the above formula (I) is usually used in a concentration of from 0.01 to 1,000 ppm, preferably from 0.3 to 500 ppm, and the concentration of folpet is usually used in a concentration of from 0.1 to 10,000 ppm, preferably from 0.5 to 5,000 ppm.

Advantageous Effects of Invention

In the composition of the present invention, the fungicidal effect against a cultivated crop infected by a plant pathogen is stable and highly active so that the composition can control a plant pathogen.

DESCRIPTION OF EMBODIMENTS

Next, preferable embodiments of an agricultural or horticultural fungicide composition of the present invention are exemplified, but the present invention should not be construed that the invention is limited to these embodiments.
(1) An agricultural or horticultural fungicide composition comprising (a) at least one imidazole compound represented by formula (I) and (b) folpet as active ingredients.
(2) The composition described in the above (1), which comprises a synergistic effective amount of (a) at least one imidazole compound represented by formula (I) and (b) folpet.
(3) The composition according to the above (1), wherein a weight ratio of (a) at least one imidazole compound represented by formula (I) to (b) folpet is 1:10,000 to 10,000:1.
(4) The composition described in the above (1), wherein a weight ratio of (a) at least one imidazole compound represented by formula (I) to (b) folpet is 1:2,000 to 2,000:1.
(5) The composition described in any one of the above (1) to (4), wherein the imidazole compound represented by formula (I) is Cyazofamid.
(6) A method for controlling a plant pathogen, comprising applying an effective amount of (a) at least one imidazole compound represented by formula (I) and an effective amount of (b) folpet to a plant or soil.

EXAMPLES

Next, Test Examples with regard to the present invention described below, but the present invention should not be construed that the invention is limited to these Examples.

Test Example 1

Inhibition Test of Mycelial Growth Against the Genus *Pythium* (*Pythium Aristosporum*)

*Pythium aristosporum* was precultured. And the obtained hyphae (4 mm in diameter) was transplanted on potato sucrose agar medium (PSA) including an agent at a predetermined concentration, and then cultured for two days at room temperature of 20° C., followed by measuring a diameter of the mycelial colony to obtain an inhibition rate of mycelial growth.

The result was shown in Table 1.

In addition, a theoretical value of the inhibition rate was calculated using Colby's formula and listed in parentheses of Table 1. If an experimental value is higher than theoretical value obtained by Colby's formula, the composition of the present invention exhibit a synergistic effect on controlling of a plant pathogen.

TABLE 1

Inhibition Rate of Mycelial Growth against *Pythium aristosporum* (%) (Theoretical Value)

| | Cyazofamid | | | | |
|---|---|---|---|---|---|
| Folpet | 100 ppm | 10 ppm | 1 ppm | 0.1 ppm | 0 ppm |
| 100 ppm | 100 (94) | 100 (94) | 100 (94) | 100 (91) | 90 |
| 10 ppm | 95 (68) | 100 (66) | 100 (66) | 81 (54) | 45 |
| 1 ppm | 48 (43) | 60 (40) | 72 (40) | 47 (20) | 3 |
| 0.1 ppm | 47 (43) | 50 (40) | 60 (40) | 35 (20) | 3 |
| 0 ppm | 41 | 38 | 38 | 17 | |

Test Example 2

Inhibition Test of Mycelial Growth Against the Genus *Pythium* (*Pythium Aphanidermatum*)

The inhibition rate of mycelial growth was obtained by measuring a diameter of mycelial colony in the same manner as Test Example 1.

The result was shown in Table 2.

In addition, a theoretical value of the inhibition rate was calculated using Colby's formula and listed in parentheses of Table 2. If an experimental value is higher than theoretical value obtained by Colby's formula, the composition of the present invention exhibit a synergistic effect on controlling of a plant pathogen.

TABLE 2

Inhibition Rate of Mycelial Growth against *Pythium aphanidermatum* (%) (Theoretical Value)

| | Cyazofamid | | | | |
|---|---|---|---|---|---|
| Folpet | 100 ppm | 10 ppm | 1 ppm | 0.1 ppm | 0 ppm |
| 100 ppm | 100 (96) | 100 (92) | 100 (90) | 100 (91) | 80 |
| 10 ppm | 100 (92) | 100 (85) | 100 (82) | 100 (83) | 62 |
| 1 ppm | 90 (80) | 88 (60) | 90 (52) | 72 (54) | 0 |

TABLE 2-continued

Inhibition Rate of Mycelial Growth against *Pythium aphanidermatum* (%)
(Theoretical Value)

| Folpet | Cyazofamid | | | | |
|---|---|---|---|---|---|
| | 100 ppm | 10 ppm | 1 ppm | 0.1 ppm | 0 ppm |
| 0.1 ppm | 82 (80) | 78 (61) | 72 (53) | 74 (55) | 2 |
| 0 ppm | 80 | 60 | 52 | 54 | |

Next, examples of the composition of the present invention described below as Formulation Examples, but the present invention should not be construed that the invention is limited to these Examples.

Formulation Example 1

| | |
|---|---|
| (1) Cyazofamid | 2 parts by weight |
| (2) Folpet | 10 parts by weight |
| (3) Sodium naphthalene sulphonate formaldehyde condensates | 5 parts by weight |
| (4) Sodium alkyl benzene sulphonate | 5 parts by weight |
| (5) Clay | 78 parts by weight |

The foregoing each component is mixed to obtain a wettable powder.

Formulation Example 2

| | |
|---|---|
| (1) Cyazofamid | 0.5 parts by weight |
| (2) Folpet | 2.5 parts by weight |
| (3) Calcium carbonate | 20 parts by weight |
| (4) Clay | 77 parts by weight |

The foregoing each component is mixed to obtain a dustable powder.

While the invention has been described in detail and with reference to specific embodiments thereof, it will be apparent to one skill in the art that various changes and modifications can be made therein without departing from the spirit and scope thereof.

This application is based on Japanese patent application No. 2009-160257 filed on Jul. 6, 2009, the entire contents of which are incorporated hereinto by reference. All references cited herein are incorporated in their entirety.

INDUSTRIAL APPLICABILITY

In the composition of the present invention, the fungicidal effect against a cultivated crop infected by a plant pathogen is stable and highly active so that the composition can control a plant pathogen.

The invention claimed is:

1. An agricultural or horticultural fungicide composition, comprising (a) at least one imidazole compound represented by formula (I):

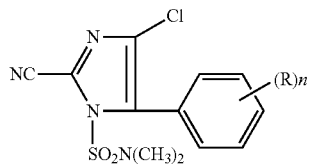

wherein R represents a C1-6 alkyl group or a C1-6 alkoxy group; and n represents an integer of 1 to 5, and (b) folpet as active ingredients, wherein a weight ratio of (a) at least one imidazole compound represented by formula (I) to (b) folpet is 1:100 to 1000:1, the amount of (a) at least one imidazole compound represented by formula (I) is from 0.1 ppm to 1,000 ppm, and the amount of (b) folpet is from 0.1 ppm to 10,000 ppm.

2. The composition according to claim 1, wherein the imidazole compound represented by formula (I) is Cyazofamid.

3. A method for controlling a plant pathogen, comprising applying the composition according to claim 1 to a plant or soil.

4. A method for controlling a plant pathogen, comprising applying the composition of claim 1 to a plant or soil.

5. A method for controlling a plant pathogen, comprising applying the composition according to claim 2 to a plant or soil.

* * * * *